(12) United States Patent
Sabir et al.

(10) Patent No.: US 9,173,674 B2
(45) Date of Patent: *Nov. 3, 2015

(54) DEVICES FOR HARVESTING A SKIN GRAFT

(75) Inventors: Sameer Ahmed Sabir, Cambridge, MA (US); Jeffrey Cerier, Cambridge, MA (US); Andrew Ziegler, Arlington, MA (US)

(73) Assignee: MoMelan Technologies, Inc., Cambridge, MA (US)

( * ) Notice: Subject to any disclaimer, the term of this patent is extended or adjusted under 35 U.S.C. 154(b) by 313 days.

This patent is subject to a terminal disclaimer.

(21) Appl. No.: 13/346,318

(22) Filed: Jan. 9, 2012

(65) Prior Publication Data

US 2012/0172894 A1    Jul. 5, 2012

Related U.S. Application Data

(63) Continuation-in-part of application No. 12/851,656, filed on Aug. 6, 2010, now Pat. No. 8,562,626.

(51) Int. Cl.
*A61B 17/322*    (2006.01)
*A61B 18/20*    (2006.01)
*A61B 18/28*    (2006.01)

(52) U.S. Cl.
CPC ............. *A61B 17/322* (2013.01); *A61B 18/203* (2013.01); *A61B 18/28* (2013.01)

(58) Field of Classification Search
CPC .. A61B 17/32; A61B 17/322; A61B 17/3205; A61B 17/3209; A61B 17/32096; A61B 17/3211; A61B 2017/32006; A61B 2017/320056; A61B 2017/320052
USPC .................. 606/131, 132, 167–172, 174, 190
See application file for complete search history.

(56) References Cited

U.S. PATENT DOCUMENTS

| | | | |
|---|---|---|---|
| 2,379,574 A | 7/1945 | Goldthwait |
| 2,721,555 A | 10/1955 | Jenny |
| 3,054,404 A | 9/1962 | Meek |
| 3,782,387 A | 1/1974 | Falabella |
| 4,345,374 A | 8/1982 | Jacobson |
| 4,600,533 A | 7/1986 | Chu |
| 4,666,447 A | 5/1987 | Smith |
| 4,679,324 A | 7/1987 | Krik |
| 4,773,418 A | 9/1988 | Hettich |

(Continued)

FOREIGN PATENT DOCUMENTS

| | | |
|---|---|---|
| CN | 101053528 A | 10/2007 |
| EP | 099748 A1 | 2/1984 |

(Continued)

OTHER PUBLICATIONS

Awad, Chinese Cupping: A Simple Method to Obtain Epithelial Grafts for the Management of Resistant Localized Vitiligo, American Society of Dermatologic Surgery, Inc., Dermatol Surg, (2008) 34(9):1186-1193.

(Continued)

*Primary Examiner* — Ahmed Farah
(74) *Attorney, Agent, or Firm* — Reza Mollaaghababa; Thomas Engellenner; Pepper Hamilton, LLP

(57) ABSTRACT

The present invention generally relates to devices for harvesting a skin graft(s). The present invention provides a blister raising device integrated with a member for cutting the blister.

22 Claims, 7 Drawing Sheets

(56) References Cited

U.S. PATENT DOCUMENTS

| | | | |
|---|---|---|---|
| 4,917,086 A | 4/1990 | Feltovich et al. | |
| 5,015,584 A | 5/1991 | Brysk | |
| 5,386,633 A | 2/1995 | Kanno | |
| 5,441,490 A | 8/1995 | Svedman | |
| 5,460,939 A | 10/1995 | Hansbrough | |
| 5,476,478 A | 12/1995 | Jackson | |
| 5,489,304 A | 2/1996 | Orgill | |
| 5,496,339 A | 3/1996 | Koepnick | |
| 5,545,222 A | 8/1996 | Bonutti | |
| 5,571,098 A | 11/1996 | Domankevitz | |
| 5,595,570 A | 1/1997 | Smith | |
| 5,686,303 A | 11/1997 | Korman | |
| 5,730,717 A | 3/1998 | Gelbfish | |
| 5,759,193 A | 6/1998 | Burbank | |
| 5,817,115 A | 10/1998 | Nigam | |
| 5,888,219 A | 3/1999 | Bonutti | |
| 5,914,264 A | 6/1999 | Korman | |
| 5,921,980 A | 7/1999 | Kiru | |
| 5,972,476 A | 10/1999 | Field | |
| 5,976,163 A | 11/1999 | Nigam | |
| 6,056,738 A | 5/2000 | Marchitto | |
| 6,063,094 A | 5/2000 | Rosenberg | |
| 6,071,247 A | 6/2000 | Kennedy | |
| 6,080,166 A | 6/2000 | McEwen et al. | |
| 6,248,114 B1 | 6/2001 | Ysebaert | |
| 6,254,580 B1 | 7/2001 | Svedman | |
| 6,358,260 B1 | 3/2002 | Ross | |
| 6,364,908 B1 | 4/2002 | Ysebaert | |
| 6,402,770 B1 | 6/2002 | Jessen | |
| 6,436,078 B1 | 8/2002 | Svedman et al. | |
| 6,585,939 B1 | 7/2003 | Dapprich | |
| 6,623,498 B1 | 9/2003 | Ziemer | |
| 6,800,282 B1 | 10/2004 | Thomson | |
| 6,860,904 B2 | 3/2005 | Bonutti | |
| 7,056,327 B2 | 6/2006 | Levesque et al. | |
| 7,078,582 B2 | 7/2006 | Stebbings | |
| 7,137,979 B2 | 11/2006 | Conrad et al. | |
| 7,207,998 B2 | 4/2007 | Feingold | |
| 7,208,006 B2 | 4/2007 | Fleischman | |
| 7,244,444 B2 | 7/2007 | Bates | |
| 7,540,875 B2 | 6/2009 | Jessen | |
| 7,625,384 B2 | 12/2009 | Eriksson | |
| 7,651,507 B2 | 1/2010 | Mishra | |
| 7,666,134 B2 | 2/2010 | Eriksson | |
| 7,666,192 B2 | 2/2010 | Seegert | |
| 7,708,746 B2 | 5/2010 | Eriksson | |
| 7,727,760 B2 | 6/2010 | Guu et al. | |
| 7,926,401 B2 | 4/2011 | Mishra | |
| 8,002,779 B2 | 8/2011 | Barker et al. | |
| 8,109,187 B2 | 2/2012 | Mishra | |
| 8,162,957 B2 | 4/2012 | Mishra | |
| 8,187,285 B2 | 5/2012 | Eriksson | |
| 8,562,626 B2 * | 10/2013 | Sabir et al. | 606/132 |
| 2001/0029380 A1 | 10/2001 | Ysebaert | |
| 2002/0052614 A1 | 5/2002 | GeBauer | |
| 2003/0009185 A1 | 1/2003 | Jessen | |
| 2003/0212357 A1 | 11/2003 | Pace | |
| 2004/0097967 A1 | 5/2004 | Ignon | |
| 2004/0172045 A1 | 9/2004 | Eriksson | |
| 2004/0186498 A1 | 9/2004 | Barnes et al. | |
| 2004/0215217 A1 | 10/2004 | Banbury | |
| 2004/0225309 A1 | 11/2004 | Eriksson | |
| 2004/0230215 A1 | 11/2004 | Eriksson et al. | |
| 2004/0237744 A1 | 12/2004 | Lin | |
| 2005/0038520 A1 | 2/2005 | Binette | |
| 2005/0101972 A1 | 5/2005 | Bhatavadekar | |
| 2005/0221276 A1 | 10/2005 | Rozakis et al. | |
| 2005/0234485 A1 * | 10/2005 | Seegert et al. | 606/172 |
| 2006/0079852 A1 | 4/2006 | Bubb et al. | |
| 2006/0141616 A1 | 6/2006 | Guu | |
| 2006/0173087 A1 | 8/2006 | Hyde et al. | |
| 2006/0258956 A1 | 11/2006 | Haberstich et al. | |
| 2006/0271070 A1 | 11/2006 | Eriksson | |
| 2006/0287696 A1 | 12/2006 | Wright et al. | |
| 2007/0183974 A1 | 8/2007 | Pearlman | |
| 2007/0255168 A1 | 11/2007 | Hibner et al. | |
| 2009/0085286 A1 | 4/2009 | Grist et al. | |
| 2010/0012311 A1 | 1/2010 | Colongo | |
| 2010/0042127 A1 | 2/2010 | Eriksson | |
| 2010/0121311 A1 | 5/2010 | Seegert et al. | |
| 2010/0145360 A1 | 6/2010 | Eriksson | |
| 2010/0152651 A1 | 6/2010 | Boyden et al. | |
| 2010/0152750 A1 | 6/2010 | Memar | |
| 2010/0286635 A1 | 11/2010 | Watson, Jr. | |
| 2010/0310823 A1 | 12/2010 | Albertelli et al. | |
| 2011/0077664 A1 | 3/2011 | Schulz | |
| 2011/0251602 A1 | 10/2011 | Anderson | |
| 2011/0264115 A1 * | 10/2011 | Asrani et al. | 606/132 |
| 2012/0021186 A1 | 1/2012 | Schneider | |
| 2012/0035599 A1 | 2/2012 | Sabir | |
| 2012/0035618 A1 | 2/2012 | Sabir | |
| 2012/0035619 A1 | 2/2012 | Sabir | |
| 2012/0035620 A1 | 2/2012 | Sabir | |
| 2012/0041430 A1 | 2/2012 | Anderson | |
| 2012/0125798 A1 * | 5/2012 | Baecker et al. | 206/524.1 |
| 2012/0136323 A1 | 5/2012 | Stasko et al. | |
| 2012/0172894 A1 | 7/2012 | Sabir | |
| 2012/0197267 A1 | 8/2012 | Sabir | |
| 2012/0201755 A1 | 8/2012 | Rozakis et al. | |
| 2012/0201793 A1 | 8/2012 | Bellomo | |
| 2012/0244623 A1 | 9/2012 | Patel | |
| 2012/0271320 A1 | 10/2012 | Hall | |
| 2013/0041385 A1 | 2/2013 | Giovannoli | |
| 2013/0145596 A1 | 6/2013 | Sabir et al. | |
| 2013/0204273 A1 | 8/2013 | Sabir et al. | |

FOREIGN PATENT DOCUMENTS

| | | |
|---|---|---|
| EP | 1614404 | 1/2006 |
| WO | 9211879 | 7/1992 |
| WO | 9528886 | 11/1995 |
| WO | 9618432 | 6/1996 |
| WO | 9633768 | 10/1996 |
| WO | 9720509 | 6/1997 |
| WO | 9816158 | 4/1998 |
| WO | 03020333 | 3/2003 |
| WO | 03039382 | 5/2003 |
| WO | 03049626 | 6/2003 |
| WO | 03049783 | 6/2003 |
| WO | 2004071313 | 8/2004 |
| WO | 2004075764 | 9/2004 |
| WO | 2004078032 | 9/2004 |
| WO | 2004105576 | 12/2004 |
| WO | 2005033273 | 4/2005 |
| WO | 2005046428 | 5/2005 |
| WO | 2007034438 A2 | 3/2007 |
| WO | 2007117488 | 10/2007 |
| WO | 2010036788 | 4/2010 |
| WO | 2011038326 | 3/2011 |
| WO | 2011059441 | 5/2011 |
| WO | 2011075676 | 6/2011 |
| WO | 2012019094 | 2/2012 |
| WO | 2012019095 | 2/2012 |
| WO | 2012019096 | 2/2012 |
| WO | 2012019098 | 2/2012 |
| WO | 2012102812 | 8/2012 |
| WO | 2012145504 | 10/2012 |

OTHER PUBLICATIONS

Balaji et al., Isolation of a Novel Population of Multipotent Stem Cells From Epidermal Layer of Human Skin, Biology and Medicine, (2010), 2(2):57-67.

Kreis et al., Expansion techniques for skin grafts: comparison between mesh and Meek Island (sandwich-) grafts, Burns, (1994), 20(1):S39-S42.

Lari et al., Expansion technique for skin grafts (Meek technique) in the treatment of severely burned patients, Burns, (2001), 27:61-66.

Mulekar et al., Treatment of Vitiligo on Difficult-to-Treat Sites Using Autologous Noncultured Cellular Grafting, Dermatol Surg., (2009), 25(1):66-71.

Meek et al., Successful Microdermagrafting Using the Meek-Wall Microdermatome, Am J Surg, (1958), 96(4):557-558.

(56) References Cited

OTHER PUBLICATIONS

International Search Report and Written Opinion dated Dec. 16, 2011 for International Application No. PCT/US11/46737, 8 pages.

International Search Report and Written Opinion dated Dec. 23, 2011 for International Application No. PCT/US11/46739, 6 pages.

International Search Report and Written Opinion dated Dec. 16, 2011 for International Application No. PCT/US11/46738, 6 pages.

International Search Report and Written Opinion dated Dec. 6, 2011 for International Application No. PCT/US11/46741, 6 pages.

Office Action dated Dec. 18, 2014 for U.S. Appl. No. 13/120,799.

European Examination Report issued Mar. 18, 2015 corresponding to European Application No. 11815368.3 (4 sheets).

Office Action issued Feb. 20, 2015 with English Text of Office Action corresponding to Japanese Patent Application No. 2013-523359 (sheets).

Office Action dated May 8, 2015 for U.S. Appl. No. 14/211,026.

International Search Report dated Oct. 2, 2014 for PCT/US2014/027205.

International Search Report dated Mar. 11, 2015 for PCT/US2014/072170.

International Search Report dated Mar. 13, 2015 for PCT/US2014/072180.

International Search Report dated Mar. 11, 2015 for PCT/US2014/072188.

BBC—GCSE Bitsize: Gore-Tex, Article: http://www.bbc.co.uk/schools/gcsebitesize/science/or_gateway_pre_2011/carbon_chem/6_designer_polyers3.shtml.

* cited by examiner

Panel A

Panel B

Panel A

Panel B

Panel C

Panel D

Panel A.

Panel B.

DEVICES FOR HARVESTING A SKIN GRAFT

REFERENCE TO RELATED APPLICATIONS

This application is a continuation in part of U.S. application Ser. No. 12/851,656, filed Aug. 6, 2010, the contents of which are herein incorporated by reference in its entirety.

FIELD OF THE INVENTION

The present invention generally relates to devices for harvesting a skin graft.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. Harvesting of a skin graft may be accomplished by many different techniques, and the technique used will depend on the type of graft to be harvested. A common technique to harvest a skin graft includes suction blistering. Suction blistering typically involves a heat source to warm the skin which facilitates blister formation.

The heat source of a suction blistering device can become overheated and burn out, causing inconsistent blister formation and potential harm to the patient. Thus, there is a need for a skin graft harvesting device with design features that prevent the device from overheating.

Current skin graft harvesting devices do not include means to monitor the development of suction blisters formation. Without such means, the device may be applied for overly long periods of time causing excessive discomfort or harm to the patient, or insufficient periods of time for causing blister formation. Thus, there is a need for a skin graft harvesting device with design features that allow the user to visually monitor the development of suction blisters on a patient.

A common technique for harvesting a skin graft includes creating one or more suction blisters, cutting the blister, and transferring the blister to a substrate, for example Tegaderm®. If the substrate is not sufficiently contacted with the suction blister, the blister won't transfer and will thus be unusable. As such, there is a need for a skin grafting device with design features that ensure full contact between the substrate and suction blister.

SUMMARY

The present invention provides devices for generating and harvesting a skin graft having improved design features for ensuring sufficient and consistent blister formation and reducing patient harm and discomfort.

In one aspect, the invention provides a device for generating and harvesting a skin graft having design features that prevent a heating element in the device from overheating and burning out. The device includes a head that contains a heating element for raising at least one blister, a hollow body configured for placement on a skin surface, at least one plate member and a cutting member, both integrated within the hollow body. Preferably, the heating element radiates heat between a temperature of about 100° C. to about 750° C. In a particular embodiment, the heating element radiates heat at a temperature of about 500° C. In certain aspects, the heating element radiates wavelengths ranging from about 10 nanometers to about 3000 nanometers, or any specific value within said range. Suitable materials for the heating element include, for example, nichrome wire.

The cutting member can be a second plate member integrated within the hollow body that is movable with respect to the other plate member(s) to cut the raised blister.

The plate member includes a surface that is configured for attenuating the reflection of heat emitted from the heating element. The surface configured for attenuating heat reflection includes a material that substantially absorbs the electromagnetic radiation emitted from the heating element contained within the head of the device. Suitable materials include, for example, thermoplastic polymers, including flouropolymers such as polytetrafluoroethylene. Preferably, the material is a dark colored material, such as a black, brown, purple or blue colored material. Alternatively, the surface that attenuates heat reflection can be electroplated, anodized, painted (e.g., a dark color such as black, brown, purple or blue) or abraded.

In a second aspect, the invention provides a device for generating and harvesting a skin graft having design features that allow a user, such as a clinician, to visually monitor blister formation. The device includes a head that contains a heating mechanism for raising at least one blister and at least one viewing window integrated within the head for monitoring blister formation. The device further includes a hollow body configured for placement on a skin surface, at least one plate member and a cutting member, both integrated within the hollow body. The cutting member can be a second plate member integrated within the hollow body that is movable with respect to the other plate member(s) to cut the raised blister.

The viewing window is preferably made of a substantially transparent material, such as an optical polymer, glass or crystal. Such materials may include an anti-fog treatment, anti-scratch coating, or anti-glare coating. In certain aspects, at least a portion of the viewing window includes a magnification lens. In another aspect, the viewing window can include at least one calibration mark for monitoring blister formation. The viewing window may simultaneously serve as an optical shield and attenuate the entrance of ambient light.

In a third aspect, the invention provides a device for generating and harvesting a skin graft having design features for monitoring blister formation that include a gauge integrated within the body of the device. The device includes a head comprising a mechanism for raising one or more blisters, a hollow body configured for placement on skin, a plate member and a cutting member integrated within the hollow body. The cutting member can be a second plate member integrated within the hollow body that is movable with respect to the other plate member(s) to cut the raised blister.

The plate member includes one or more holes through which the one or more blisters are raised, and a gauge integrated within the plate for monitoring blister formation within the one or more holes. The holes have a depth substantially equal to the thickness of the plate member. The gauge is proximal to one or more of the holes through which the blisters are raised. In certain aspects, the gauge is a counterbore within one or more of the holes in the plate member. The counter bore can be about one-half to three-quarters of the depth of the hole. Alternatively, the gauge is a calibration mark proximal to one or more of the holes in the plate member. For example, the calibration mark can be laser etched or painted onto the plate next to one or more holes, or on the inner wall of one or more holes within the plate.

In a fourth aspect, the invention provides a device for generating and harvesting a skin graft having design features for improving heat transfer to facilitate blister formation. Such devices include a head that contains a heating mechanism for raising at least one blister, and a transparent or translucent surface distal to the heating mechanism for transferring heat from the heating mechanism to the body of the device. The device further includes further includes a hollow body configured for placement on a skin surface, at least one plate member and a cutting member, both integrated within the hollow body. The cutting member can be a second plate member integrated within the hollow body that is movable with respect to the other plate member(s) to cut the raised blister.

The transparent or translucent surface is preferably made of a material that allows light having a wavelength between about 10 nanometers to about 3000 nanometers to be transmitted therethrough (e.g., about 180 nm to about 2500 nm). Suitable materials include, for example, crystalline materials such as, sapphire, quartz, silicon, garnet, sillenite, fused quartz, titanium dioxide, zinc selenide, calcium fluoride, barium fluoride, zinc sulphide, caesium iodide, germanium, thallium bromo-iodide, lithium fluoride, magnesium fluoride, potassium bromide, sodium chloride, or strontium fluoride; or glass materials such as silica glass, fused silica, fluoride glass, aluminosilicate glass, phosphate glass, borate glass, chalcogenide glass, or a polymer glass.

In certain aspects, the head of the device includes two transparent or translucent surfaces distal to the heating mechanism, configured such that the two surfaces contain an airspace inbetween. The two surfaces can be made of the same material, or different materials. In a particular embodiment, the two surfaces are both a glass material.

In a fifth aspect, the invention provides a device for generating and harvesting a skin graft having design features for ensuring the capture and transfer of blisters onto a substrate. Such devices include a mechanism for raising at least one blister, a hollow body configured for placement on skin, at least one plate member integrated within the body and including at least one hole through which the blister is raised, a substrate removably coupled to the plate member, and a substrate compression mechanism movably coupled to the body. The substrate compression mechanism includes an actuator member coupled to a compression member. Actuation of the compression mechanism removably couples the compression member onto the substrate to ensure full contact between the substrate and the raised blister.

The device further includes a cutter member integrated within the body for cutting the blister. The cutting member can be a second plate member integrated within the hollow body that is movable with respect to the other plate member(s) to cut the raised blister. The device is configured such that the blister is attached to the substrate upon cutting the blister.

The compression member is movably coupled to the hollow body via an axle, a hinge, or similar mechanism that allows the compression member to be removably applied to the substrate. The actuation member can be a handle coupled to the compression member to facilitate application of the compression member to the substrate.

The compression member can be substantially the same size and shape as the substrate. For example, the compression member can be substantially square or rectangular in shape having the same dimensions as the substrate. Alternatively, the compression member can be cylindrical in shape and configured to roll along the surface of the substrate when actuated. For example, a cylindrical compression member can be configured to rotate about the longitudinal axis of a movable arm, whereby actuation of the arm in a horizontal direction translates into rotation of the compression member about the arm to roll the cylindrical member across the substrate The compression member can be made of any substantially solid material, such as any elemental metal, metal alloy, glass, crystal or polymer. The compression member is preferably reusable. However, in certain aspects, the compression member can be disposable.

While several improved design features have been individually described, such features are not mutually exclusive of each other. Any combination of design features disclosed herein can be used integrated into the devices of the invention. These design features and other aspects of the devices of the invention are described in the figures, description and claims that follow.

DETAILED DESCRIPTION

The present invention generally relates to a single device that can raise a blister (e.g., a suction blister) and cut the raised blister, i.e., a blister raising device integrated with a cutting member. Such devices are useful for harvesting skin grafts.

Figure 2:
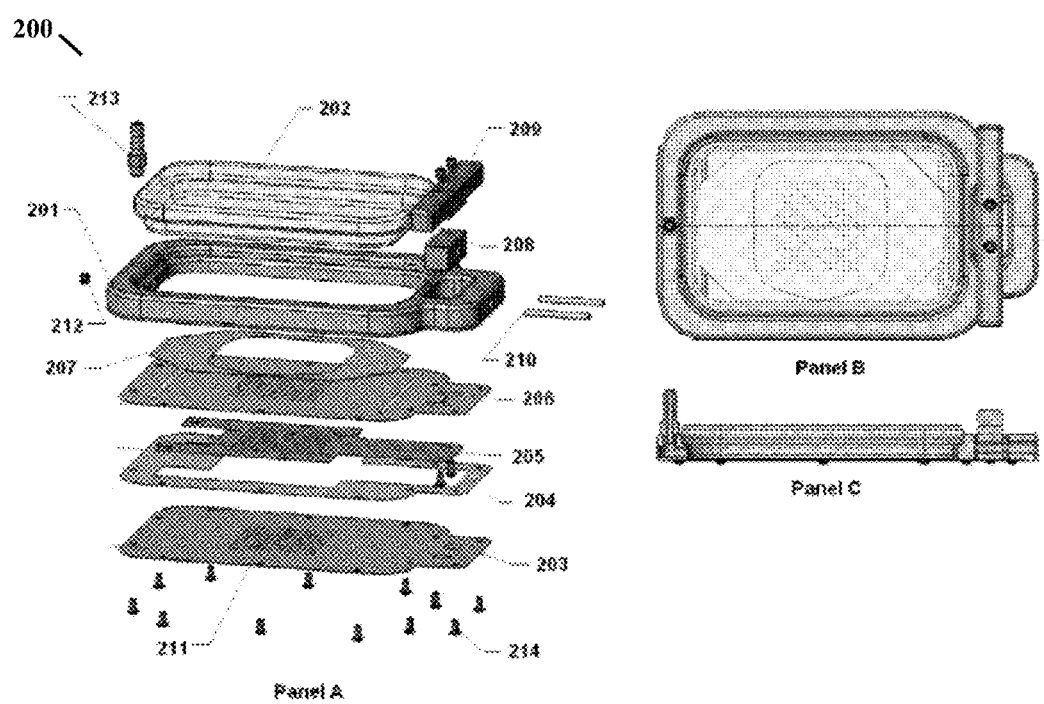
FIG. 2 panels A-C are schematics showing a device for generating and harvesting a plurality of micrografts. Panel A provides an exploded view of the device. Panel B provides a top view of the assembled device. Panel C provides a side view of the assembled device.

In certain embodiments, a device as shown in FIG. 2 panels A-C is used to raise and cut a plurality of skin grafts. Device 200 includes a frame 201 and a lid 202. Fitted into the frame is a bottom plate 203, a cutter grid plate 204, a cutter plate 205, and a top plate 206. The bottom plate 203, the cutter plate 205, and the top plate 206, each include a hole array 211. Once assembled, the hole array 211 of each of plates 203, 205, and 206 are aligned. The size of the holes in the hole array will depend on the size of the graft needed, with larger holes being used to produce larger grafts. A first substrate 207 interacts with the top plate 206 and will receive the harvested grafts.

Device 200 further includes an actuation block 208, actuation bar 209, and actuation block guides 210. Actuation components 208, 209, and 210 control movement of the cutter plate 205. The frame 201 includes a vacuum stop 212 and the lid 202 includes a suction hole barb 213. Once assembled, the frame 201 and lid 202 are arranged such that the vacuum stop 212 and the suction hole barb 213 are aligned with each other (FIG. 2 panel B). A vacuum source is then connected to the device 200 such that negative pressure can be generated within the device. The device 200 can be held together by clamp screws 214. Device 200 may also include a heating element.

To produce and harvest the plurality of skin grafts, device 200 is placed on a donor site, such as an inner thigh of a patient. The vacuum source is turned on, producing negative pressure within device 200. The negative pressure causes the skin to be pulled toward lid 202, with a plurality of different portions of skin being pulled through each hole array 211 in each of plates 203, 205, and 206. Such action results in generation of many microblisters. Once the microblisters are raised, actuation components 208, 209, and 210 are engaged to move cutter plate 205. The movement of cutter plate 205 disrupts the alignment of the hole arrays 211 in each of plates 203, 205, and 206, and results in cutting of the microblisters. The cut microblisters are captured on the first substrate 207 that is above top plate 206. In this manner, there is provided a spaced apart array of micrografts. The amount of negative pressure applied, the amount of time the vacuum is maintained, and/or the depth of the holes in plate 206 (i.e., the plate thickness) determine what type of graft will be harvested, e.g., epidermal graft, split thickness graft, or full thickness graft. Generally, each micrograft will have a lateral dimension of less than about 2 mm e.g., 100 to 2000 microns.

Another aspect of the invention provides a device for obtaining a single skin graft. Such devices of the invention include a hollow body having a distal end configured for placement on skin, a mechanism for raising a blister, and a cutter integrated in the body for cutting the blister produced on the skin.

A gauge for monitoring blister formation can be incorporated within one or more plates 203, 205, and 206. The gauge is preferably proximal to one or more holes of hole array 211 through which the blisters are formed. For example, the gauge can be located on the plate next to one or more holes of hole array 211, or on an inner wall of one or more holes of hole array 211. The gauge can be configured to provide minimum indicator of a sufficient height or dimension for a blister to be cut, and/or a maximum indicator of a sufficient blister dimension to avoid excessive patient discomfort by application of the device beyond a necessary period of time.

Each hole within the hole array has a depth substantially equal to the thickness of the plate. In certain embodiments, the gauge is a counterbore through one or more of the holes within hole array 211. The counter bore serves as a marker to indicate to the user (e.g., clinician) when the blister has reached a dimension sufficient to be cut. The counterbore can be approximately one-half to three-quarters of the depth of the hole as measured from the bottom or distal-most surface of the plate (i.e., the surface closest to the skin). For example, if the plate is 0.3 inches thick, the counter bore is 0.15 inches to 0.225 inches, as measured from the bottom or distal-most surface of the plate.

Alternatively, the gauge can be one or more calibration marks located proximal to or within one or more holes through which the blisters are raised. For example, the calibration marks can be one or more lines having a known length that are drawn, painted or etched onto the surface of the plate proximal to one or more of the holes. For example the one or more lines have a length of about 0.1 mm, about 0.2 mm, about 0.3 mm, about 0.4 mm, about 0.5 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm. Alternatively, at least two calibration marks can be drawn, painted or etched onto the surface of the plate proximal to one or more of the holes, and the distance between the at least two calibration marks can be a known length, for example about 0.1 mm, about 0.2 mm, about 0.3 mm, about 0.4 mm, about 0.5 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm. As the blister is formed, the lateral dimension of the blister can be compared to the one or more calibration marks to gauge when the blister is ready to be cut.

In yet another embodiment, the calibration marks may be one or more markings that are drawn, painted or etched onto the inner wall of one or more holes within hole array 211 of the plates. Such markings can indicate a minimum depth within the hole that is sufficient for a blister to be cut, and a maximum level for sufficient blister formation to avoid excessive patient discomfort by application of the device beyond a necessary period of time.

Figure 3:
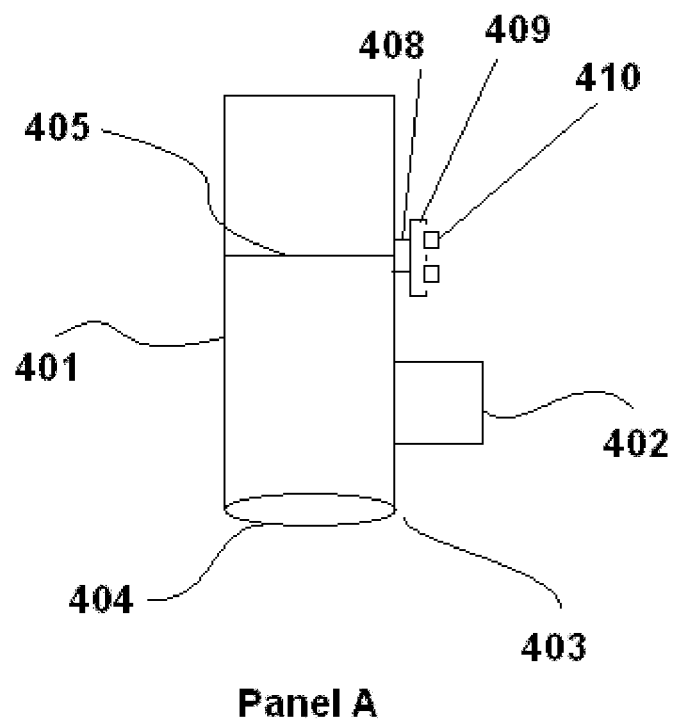
FIG. 3 panels A-B is a drawing showing a device of the invention for raising a suction blister.
Figure 3:
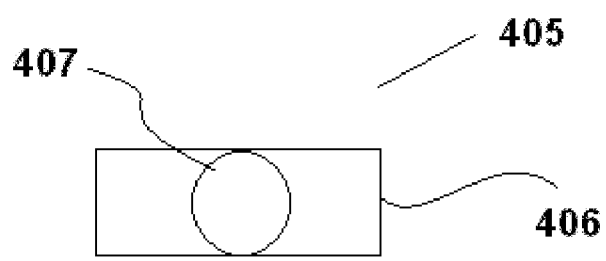

In certain embodiments, a device as shown in FIG. 3 panel A is used to obtain a skin graft. Device 400 includes a hollow body 401 and a mechanism for raising a blister 402. Hollow body 401 includes a distal end 403 that is configured for placement on the skin. Such a distal end may include an orifice plate 404. Orifice plate 404 determines the size and the shape of the blister or blisters that will be raised. Orifice plate 404 may be any shape or size and will depend on the blister to be raised. Generally, the diameter or lateral dimension of the blister may be from about 6 mm to about 12 mm, although larger or smaller blister sizes may be used.

The mechanism for raising a blister may be a vacuum component, a heating component, or a combination thereof. An exemplary heating component is a light source. In a particular embodiment, mechanism 402 is a combination of a vacuum component and a heating component.

The hollow body 401 further includes a cutter 405, which includes cutter plate 406 and a hole 407 (FIG. 3 panel B). Device 400 further includes an actuation block 408, actuation bar 409, and actuation block guides 410. Actuation components 408, 409, and 410 control movement of the cutter 405.

Blister formation is accomplished by attaching the distal end 403 of hollow body 401 to donor site of a patient, such as an inner thigh of a patient. Hook and loop fastener straps may be used to keep the device in place. The heating component of blister raising mechanism 402 provides a slight warming of orifice plate 404, which is in direct contact with the patient's skin surface. The application of a moderate negative pressure to the chamber interior from the vacuum component of blister raising mechanism 402, results in the patient's skin being gently drawn through the opening in orifice plate 404. The result is a blister or blisters, approximately the size of the opening in orifice plate 404. The produced blister may be fluid-filled or may not contain any fluid, i.e., a blister having air within. The skin and blister area is generally not damaged and patient discomfort is minimal.

The cutter 405 is positioned in hollow body 401 such that upon raising the blister, at least a portion of the blister protrudes through hole 407 in cutter plate 406. The actuation components 408, 409, and 410 are engaged to move cutter plate 406. The movement of cutter plate 406 disrupts the alignment of hole 407 with the other components of device 400, and results in cutting of the raised blister.

Preferably, the blister raising mechanism 402 is capable of emitting heat ranging between about 100° C. to about 750° C. (e.g., about 500° C.). In certain aspects, the blister raising mechanism 402 emits electromagnetic radiation having a wavelength ranging between about 10 nm and about 3000 nm. In certain aspects, electromagnetic radiation emitted from blister raising mechanism 402 is reflected off one or more of the surfaces within the device, back to mechanism 402, causing it to overheat and burnout. To prevent overheating of mechanism 402, at least one plate of plates 203, 205, and 206 and/or orifice plate(s) 404 can include at least one surface configured for attenuating the reflection of electromagnetic radiation emitted from mechanism 402. Preferably such surface is the surface facing mechanism 402 when the device is fully assembled.

For example, at least one surface of one or more of plate members 206, 205, 203 and/or orifice plate 404 can be coated with a material that substantially attenuates reflection of the electromagnetic radiation (e.g., by absorbing) emitted from mechanism 402. Suitable materials include, for example, a thermoplastic polymer coating. In a particular embodiment, the thermoplastic polymer is a fluoropolymer such as polytetrafluoroethylene. Preferably, the coating material is a dark color such as a substantially black, brown, blue or purple color.

Alternatively, one or more of plate members 206, 205, 203 and/or orifice plate 404 can be anodized, electroplated or painted a dark color such as black, brown, blue or purple to attenuate the reflection (e.g., absorb) of electromagnetic radiation emitted from mechanism 402.

In yet another embodiment one or more of plate members 206, 205, 203 and/or orifice plate 404 can be abraded, scuffed, brushed, or the like, to minimize or remove a glossy or shiny surface appearance in order to attenuate reflection of electromagnetic radiation from mechanism 402.

Figure 4:
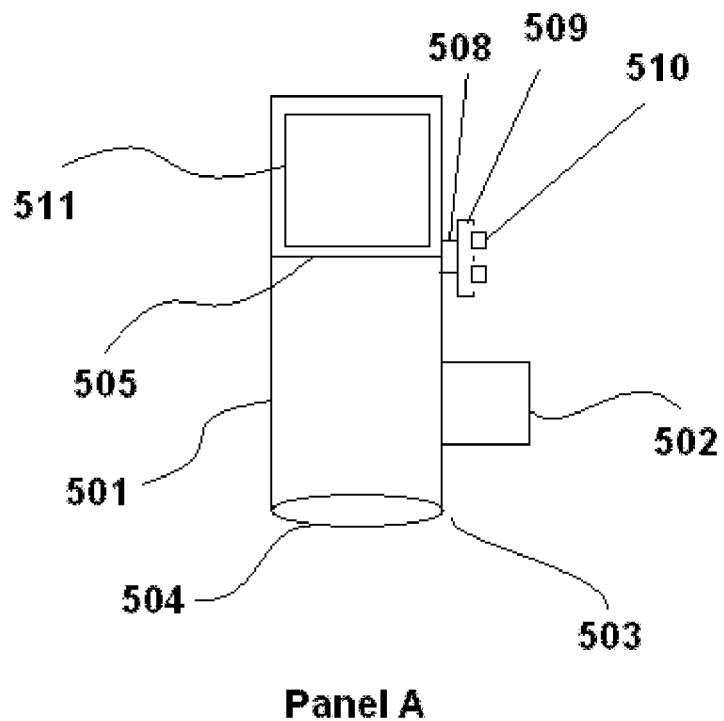
FIG. 4 panels A-D show different devices of the invention for raising a suction blister.
Figure 4:
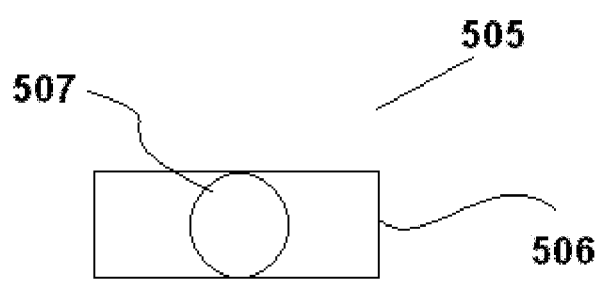
Figure 4:
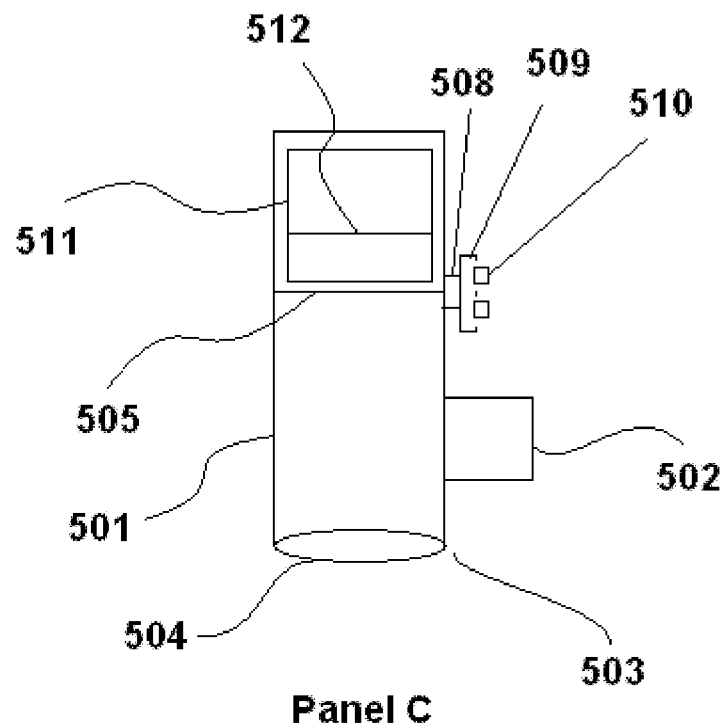
Figure 4:
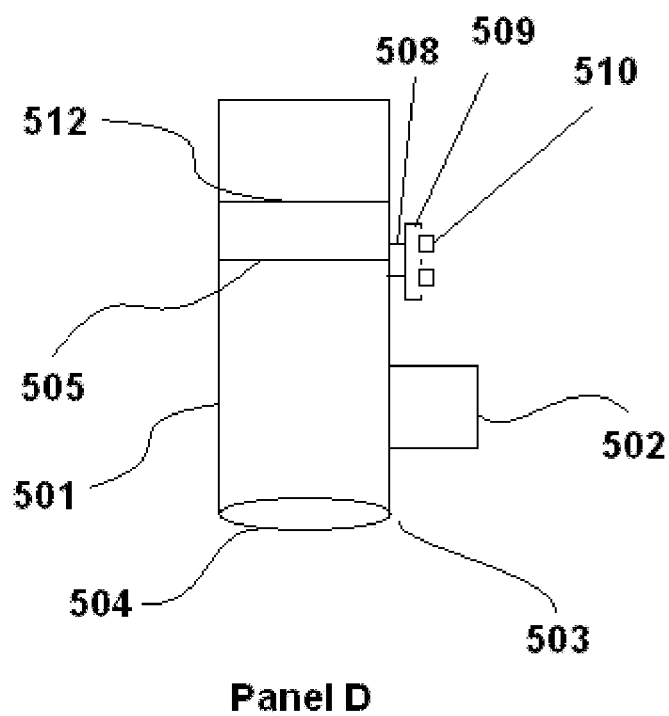

FIG. 4 panel A shows a device 500 that further includes a chamber 511 for capturing the cut blister. Chamber 511 is positioned in hollow body 501 and above cutter 505. Chamber 511 may be removable from device 500. Chamber 511 may include multiple configurations. For example, chamber 511 may include a retractable bottom. The bottom is in an open position when chamber 511 is inserted into hollow body 501. In the open position, chamber 511 is able to receive the cut blister. Once the cut blister is in chamber 511, the bottom of the chamber is closed, capturing the blister in chamber 511. Chamber 511 may then be removed from device 500.

In another embodiment, chamber 511 includes a substrate 512 (FIG. 4 panel C). In this embodiment, device 500 is configured such that substrate 512 is positioned in chamber 511 so that upon raising the blister, a portion of the blister contacts the substrate and becomes attached to the substrate. Cutter 505 then cuts the blister, and the cut blister becomes attached to the substrate 512 in chamber 511. Chamber 511 is then removed from device 500, and substrate 512 may be removed from chamber 511. In other devices, a vacuum, instead of a substrate, is used to hold the cut blister within the chamber.

In certain embodiments, device 500 does not use a chamber, rather a substrate 512 is directly integrated with device 500 in order to capture the cut blister (FIG. 4, panel D). Once captured, substrate 512 having an attached cut blister may be removed from device 500.

In certain embodiments, the device 500 includes a substrate compression mechanism for pressing the substrate against the blister to ensure that the entire blister surface contacts the substrate 512. Full contact between the entire blister surface and the substrate ensures transfer of the blister onto the substrate when the blisters are cut. In certain embodiments, the compression member is movably coupled to an exterior surface of the hollow body and actuated by an actuation member coupled to the compression member.

The compression member can be a plate having approximately the same size and shape as substrate 512. The plate can be coupled to the hollow body via a hinged mechanism or axle member and is actuated by an extension arm or handle fixedly attached to the plate. The extension arm/handle is engineered to apply at least about 2×, at least about 3×, at least about 4×, at least about 5×, at least about 6×, at least about 7×, at least about 8×, at least about 9×, at least about 10×, at least about 15×, at least about 20×, at least about 25×, at least about 30×, at least about 35×, at least about 40×, at least about 50×, at least about 75×, at least about 100× the pressure applied to the extension arm/handle onto the plate.

Alternatively, the compression mechanism can be a cylindrical roller disposed about an actuation arm that defines a longitudinal axis. Movement of the arm in a lateral direction translates into rotational movement of the cylinder about the longitudinal axis of the arm, such that the cylinder is rolled across the surface of the substrate 512 to press the substrate against the blisters.

The compression member and/or actuation member are preferably reusable. Alternatively, the compression member and/or actuation member are made of a disposable material. Materials for the construction of the compression plate or cylinder can be any substantially solid material such as an elemental metal, a metal alloy, a glass, a crystal, or a polymer. In certain embodiments, the compression member and/or actuation member are made of titanium or stainless steel.

Figure 5:
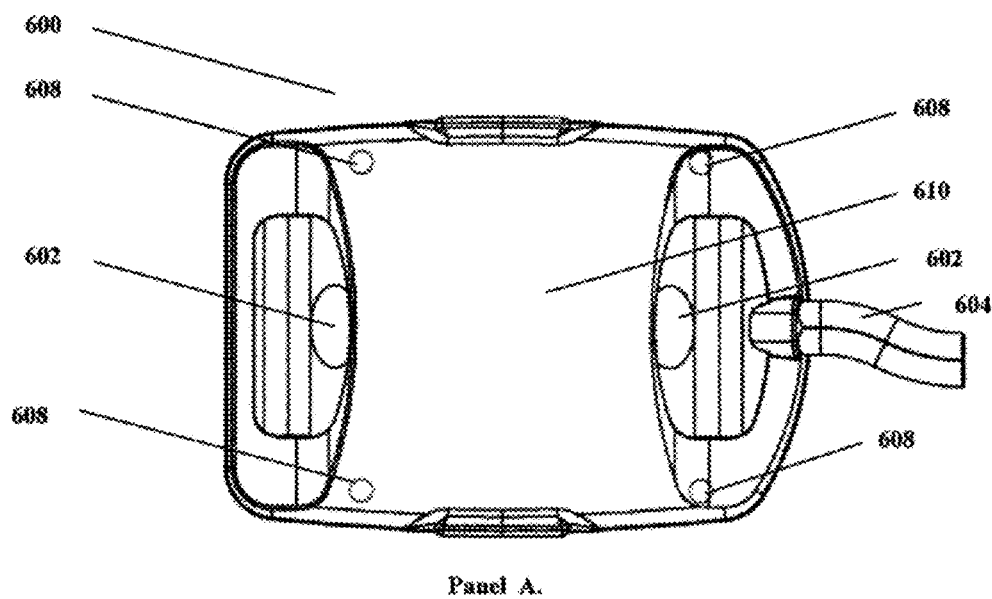
FIG. 5 panels A-B show schematics of head of a device according to the invention. Panel A provides a top view of the head. Panel B shows a side view of the head.
Figure 5:
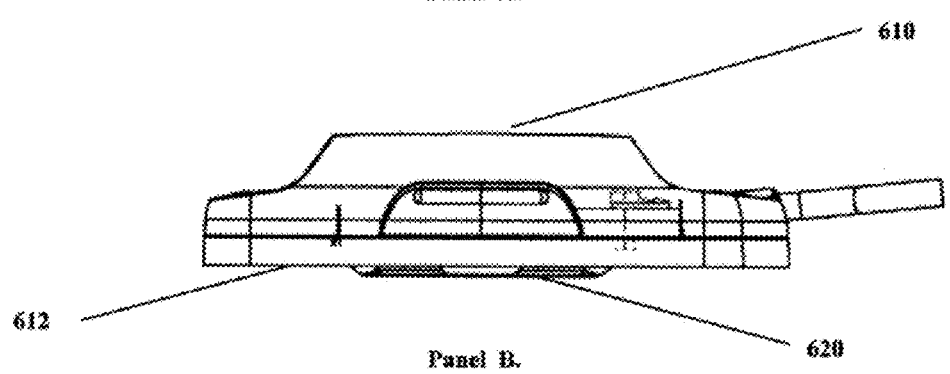
Figure 6:
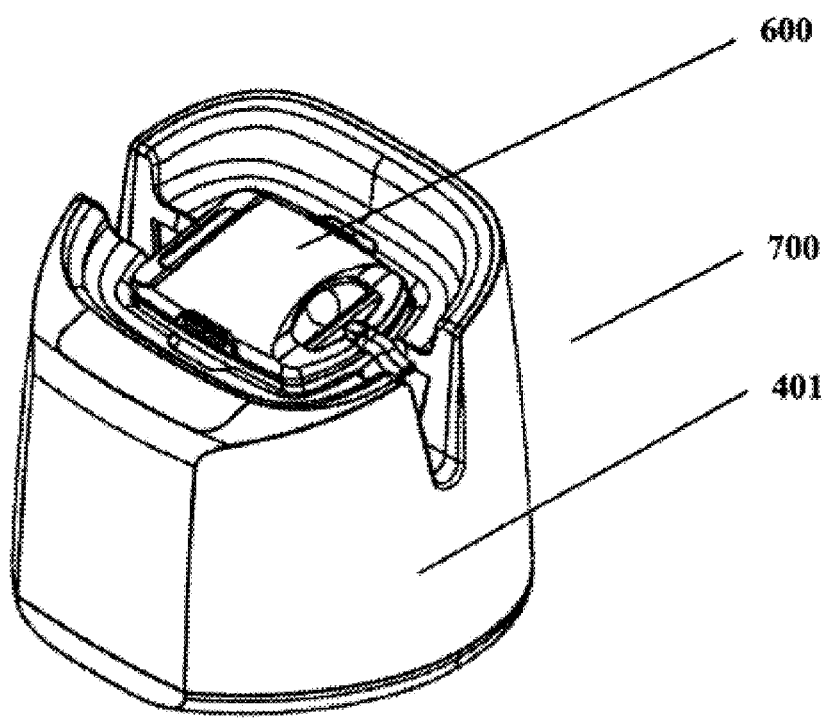
FIG. 6 provides a diagram showing an external schematic of a device with a head coupled to a hollow body.

In certain embodiments, the devices according to the invention include a head portion that can be removably coupled with the hollow body 401 of the device. FIG. 5 shows an exemplary embodiment of a removable head 600 that includes a blister raising mechanism 402 (e.g., a heating element) for raising a suction blister. The head 600 includes a topmost, proximal portion 610, and a distal portion 620 that couples with the hollow body of the device. The head 600 is coupled to the hollow body 401 via holes 608. After attachment of head 600 to the hollow body 401, a vacuum source can be attached to suction tubing 604 to generate negative pressure within the hollow body of the device. FIG. 6 shows head 600 coupled to hollow body 401 (collectively 700).

In certain embodiments, the head device includes one or more viewing windows 602. The viewing windows are located to provide optimal viewing of blister formation within the hollow body of the device. As shown in FIG. 5, a plurality of viewing windows 602 can be integrated within the head 600 to allow for alternative views of blister formation, or allow more than one user to monitor the development of the blisters. In certain embodiments, an ocular shield circumscribes the viewing lens such then when the user is viewing blister formation, the shield attenuates entrance of ambient light into the viewing lens.

The viewing window 602 can be made of any transparent material. In preferred embodiments, the viewing window 602 is comprised of optical quality material, for example an optical polymer, an optical glass, or an optical crystal. Such materials can further include one or more of an anti-fogging material, an anti-scratch coating, or an anti-glare coating, located on either the or both the interior surface, the exterior surface, or both.

In certain embodiments, the viewing window is made of a heat resistant optical polymer, optical glass, or optical crystal to prevent warping or distortion from the heating element of the blister raising mechanism 402 within the head 600.

At least a portion of the viewing window 602 can further include a magnification lens to facilitate viewing of the blisters during formation. The magnification power of the lens can be at least about 2×, at least about 3×, at least about 4×, at least about 5×, at least about 6×, at least about 7×, at least about 8×, at least about 9×, at least about 10×, at least about 15×, at least about 20×, at least about 25×, at least about 30×, at least about 35×, at least about 40×, at least about 50×, at least about 75×, at least about 100×.

In still other embodiments, the viewing window 602 can include one or more calibration marks etched or painted on the viewing window 602 for monitoring blister formation. Where the viewing window 602 includes a magnification lens, the calibration marks can be calibrated to the magnification power of the lens to approximate the actual dimensions of the forming blister, such as the actual height, the actual diameter, or both. When the desired blister size is formed as gauged by the calibration marks, the blisters are cut.

As previously described, the head 600 can include a mechanism for raising a blister 402. Such mechanism typically includes a heating element, such as nichrome wire, and is located in the topmost, proximal portion 610 of head 600

In certain embodiments of invention, head 600, includes a transparent or a translucent surface 620 forming the distal side 612 of the head 600 (i.e., distal to the heating element). The transparent or translucent surface is made of a material that facilitates the transmission of electromagnetic radiation emitted from the heating element within head 600 to one or more plate members incorporated within the hollow body, thereby warming the plate members and subsequently the skin surface.

In certain aspects, the transparent or translucent surface is made of material that allows light having a wavelength between about 10 nanometers to about 3000 nanometers to be transmitted through the surface. Suitable materials for transmission of light within such range includes, for example, crystalline materials such as sapphire, quartz, silicon, garnet, sillenite, fused silica, fused quartz, titanium dioxide, zinc selenide, calcium fluoride, barium fluoride, zinc sulphide, caesium iodide, germanium, thallium bromo-iodide, lithium fluoride, magnesium fluoride, potassium bromide, sodium chloride, or strontium fluoride. The crystalline material can polarized.

Other suitable materials include glass such as silica glass, fluoride glass, aluminosilicate glass, phosphate glass, borate glass, chalcogenide glass, or polymer glass. The glass can be polarized.

In certain aspects, the head 600 includes two transparent or translucent surfaces 620 forming the distal side 612 of head 600. The two plates surfaces are in a stacked configuration with an airspace in between them. The airspace between the transparent or translucent surfaces is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 2.0 mm, about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, about 15.0 mm, about 16.0 mm, about 17.0 mm, about 18.0 mm, about 19.0 mm, about 20.0 mm, about 21.0 mm, about 22.0 mm, about 23.0 mm, about 24.0 mm, or about 25.0 mm.

The two transparent or translucent surfaces can be the same materials, or different materials. For example, the two surfaces can both be made of a glass or crystalline material. Alternatively, one of the surfaces is a glass material, while the other surface is a crystalline material.

Figure 1:
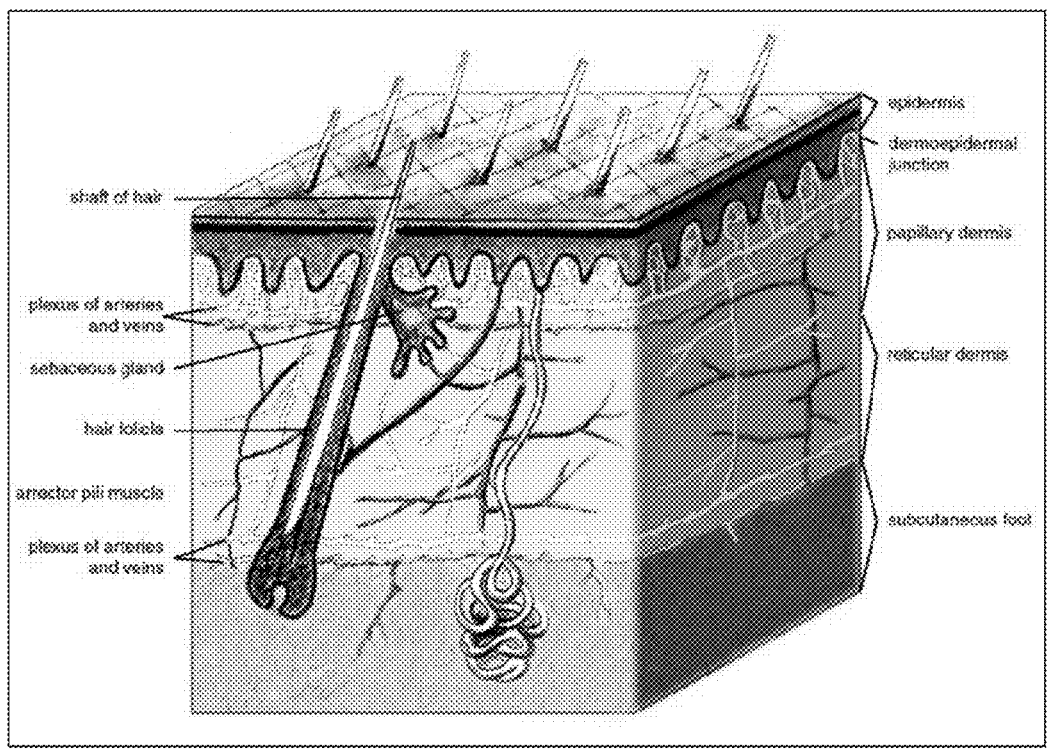
FIG. 1 provides a diagram showing the anatomy of skin.

In certain embodiments, devices of the invention are configured to produce epidermal grafts. The skin consists of 2 layers. The outer layer, or epidermis, is derived from ectoderm, and the thicker inner layer, or dermis, is derived from mesoderm. The epidermis constitutes about 5% of the skin, and the remaining 95% is dermis. FIG. 1 provides a diagram showing the anatomy of skin. The skin varies in thickness depending on anatomic location, gender, and age of the individual. The epidermis, the more external of the two layers, is a stratified squamous epithelium consisting primarily of melanocytes and keratinocytes in progressive stages of differentiation from deeper to more superficial layers. The epidermis has no blood vessels; thus, it must receive nutrients by diffusion from the underlying dermis through the basement membrane, which separates the 2 layers.

The dermis is a more complex structure. It is composed of 2 layers, the more superficial papillary dermis and the deeper reticular dermis. The papillary dermis is thinner, including loose connective tissue that contains capillaries, elastic fibers, reticular fibers, and some collagen. The reticular dermis includes a thicker layer of dense connective tissue containing larger blood vessels, closely interlaced elastic fibers, and coarse, branching collagen fibers arranged in layers parallel to the surface. The reticular layer also contains fibroblasts, mast cells, nerve endings, lymphatics, and some epidermal appendages. Surrounding the components of the dermis is the gel-like ground substance composed of mucopolysaccharides (primarily hyaluronic acid), chondroitin sulfates, and glycoproteins.

In a graft, the characteristics of the donor site are more likely to be maintained after grafting to a recipient site as a function of the thickness of the dermal component of the graft. However, thicker grafts require more favorable conditions for survival due to the requirement for increased revascularization. It has been discovered, however, that a substantially epidermal graft according to the invention is more likely to adapt to the characteristics of the recipient site.

An epidermal graft refers to a graft that consists of substantially epidermal skin and does not include any substantial portion of the dermal layer. A split thickness graft refers to a graft that includes sheets of superficial (epithelial) and some deep layers (dermal) of skin. A full-thickness graft refers to a graft that includes all of the layers of the skin including blood vessels.

Devices of the invention may be used to harvest a skin graft(s) for repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

In particular embodiments, the skin graft(s) are used to treat vitiligo. Vitiligo is a chronic disorder that causes depigmentation of patches of skin. It occurs when melanocytes, the cells responsible for skin pigmentation, die or are unable to function. Although patches are initially small, they often enlarge and change shape. When skin lesions occur, they are most prominent on the face, hands and wrists. Some lesions have hyper-pigmentation around the edges. Depigmentation is particularly noticeable around body orifices, such as the mouth, eyes, nostrils, genitalia and umbilicus.

Vitiligo is generally classified into two categories, non-segmental vitiligo and Segmental vitiligo. In non-segmental vitiligo (NSV), there is usually some form of symmetry in the location of the patches of depigmentation. New patches also appear over time and can be generalized over large portions of the body or localized to a particular area. Vitiligo where little pigmented skin remains is referred to as *vitiligo universalis*. Non-segmental vitiligo can come about at any age, unlike segmental vitiligo which is far more prevalent in teenage years.

Segmental vitiligo (SV) differs in appearance, aetiology and prevalence from associated illnesses. Its treatment is different from that of non-segmental vitiligo. It tends to affect areas of skin that are associated with dorsal roots from the spine. It spreads much more rapidly than non-segmental vitiligo and, without treatment, it is much more stable/static in course and not associated with auto-immune diseases.

To treat vitiligo, an autograft is provided to the site of depigmented skin. The graft includes melanocytes, and thus upon the recipient site accepting the graft, the graft will produce pigmented skin at the recipient site. A donor site of pigmented skin is aseptically cleaned prior to harvesting of a skin graft. Standard methods are used to clean the donor site. A typical donor site is an inner thigh, but any area of pigmented skin may be used.

After cleaning, a skin grafted is harvested using devices of the invention. Devices described herein raise and cut a blister(s), such as a suction blister. The area of depigmented skin (i.e., the recipient site), is prepared through aseptic cleaning and dermabrasion. The graft(s) is applied to the dermabraded recipient site. The donor site and the recipient site are dressed and wound care is provided.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for obtaining a skin graft, the device comprising:
   a head comprising a mechanism for raising at least one blister;
   at least one viewing window integrated within said head for monitoring blister formation;
   a hollow body having a distal end configured for placement on a skin surface;
   at least one plate member integrated within said body comprising at least one hole through which said blister is raised; and
   a cutting member integrated in said body for cutting said blister;
   wherein said head is configured for removable coupling with said hollow body, said head being further configured for coupling to a vacuum source for generating a negative pressure within the hollow body for forming the blister.

2. The device of claim 1, wherein said cutting member is a second plate member.

3. The device according to claim 2, wherein at least one of the plates is movable with respect to the other thereby to perform a cutting action.

4. The device of claim 1, wherein said viewing window comprises a transparent material.

5. The device of claim 4, wherein said transparent material is selected from the group consisting of an optical polymer, an optical glass, and an optical crystal.

6. The device according to claim 1, wherein at least a portion of said viewing window further comprises a magnification lens.

7. The device according to claim 6, wherein said magnification lens magnifies objects at a magnification ranging from about 2× to about 100×.

8. The device according to claim 6, wherein at least a portion of said viewing window comprises an ocular shield circumscribing said magnification lens and configured for attenuating entrance of ambient light into said magnification lens.

9. The device according to claim 6, wherein said viewing window comprises one or more calibration marks calibrated to a magnification power of the lens to indicate one or more dimensions of said at least one blister.

10. The device according to claim 9, wherein said one or more dimensions comprise any of height, diameter of the blister.

11. The device according to claim 1, wherein said viewing window comprises one or more materials selected from an anti-fogging material, an anti-scratch coating, and an anti-glare coating.

12. The device according to claim 1, wherein said viewing window comprises a heat resistant material.

13. The device according to claim 1, wherein said viewing window comprises one or more calibration marks for monitoring formation of said blister.

14. The device according to claim 1, further comprising:
   a substrate removably coupled to said plate member; and
   a substrate compression mechanism movably coupled to said body, said compression mechanism comprising an actuator member coupled to a compression member, whereby actuation of said compression mechanism removably couples said compression member onto said removable substrate;
   the device configured such that the blister is attached to the substrate upon cutting said blister.

15. The device according to claim 14, wherein said compression member is a plate having the same dimension as the substrate.

16. The device according to claim 15, wherein said compression member plate is coupled to an external portion of said hollow body via a hinge or axle mechanism.

17. The device according to claim 14, wherein said compression member is cylindrical in shape.

18. The device according to claim 17, wherein said cylindrical compression member is axially disposed about a movable arm defining a longitudinal axis, whereby lateral movement of said arm rotates the cylindrical member about the longitudinal axis of said arm, and wherein actuation of the movable arm translates into rotational movement of the cylindrical member on the substrate.

19. The device according to claim 14, wherein said compression member is disposable.

20. The device according to claim 14, wherein said compression member is reusable.

21. The device according to claim 14, wherein said compression member is removably coupled to said actuating member.

22. The device according to claim 14, wherein said compression member is comprised of an elemental metal, a metal alloy, a glass, a crystal, or a polymer.

* * * * *